US008566735B2

(12) United States Patent
Takemura et al.

(10) Patent No.: US 8,566,735 B2
(45) Date of Patent: Oct. 22, 2013

(54) HARDNESS TESTER WITH A USER INTERFACE FOR SETTING TEST LOCATIONS

(75) Inventors: Fumihiro Takemura, Kawasaki (JP); Kozo Ariga, Tokyo (JP)

(73) Assignee: Mitutoyo Corporation, Kanagawa (JP)

( * ) Notice: Subject to any disclaimer, the term of this patent is extended or adjusted under 35 U.S.C. 154(b) by 271 days.

(21) Appl. No.: 13/238,014

(22) Filed: Sep. 21, 2011

(65) Prior Publication Data

US 2012/0087567 A1      Apr. 12, 2012

(30) Foreign Application Priority Data

Oct. 6, 2010   (JP) .................................. 2010-226292

(51) Int. Cl.
*G01N 3/48* (2006.01)
*G06F 3/048* (2013.01)
*G01N 3/42* (2006.01)
*G06F 9/44* (2006.01)

(52) U.S. Cl.
CPC ................ *G01N 3/42* (2013.01); *G06F 9/4443* (2013.01)
USPC ........ 715/765; 73/78; 73/81; 73/82; 715/764; 715/810

(58) Field of Classification Search
USPC .......................... 73/78–85; 715/764, 765, 810
See application file for complete search history.

(56) References Cited

U.S. PATENT DOCUMENTS

| 4,627,096 | A | * | 12/1986 | Grattoni et al. ................ 382/141 |
| 5,146,779 | A | * | 9/1992 | Sugimoto et al. .................. 73/81 |
| 5,284,049 | A | * | 2/1994 | Fukumoto ......................... 73/82 |
| 7,121,136 | B2 | * | 10/2006 | Tsujii et al. ........................ 73/81 |
| 7,380,443 | B2 | * | 6/2008 | Tsujii et al. ........................ 73/81 |
| 2004/0096093 | A1 | * | 5/2004 | Hauck et al. .................. 382/141 |
| 2004/0134263 | A1 | * | 7/2004 | Tsujii et al. ........................ 73/81 |
| 2005/0081608 | A1 | * | 4/2005 | Shoelson ........................ 73/105 |
| 2006/0288763 | A1 | * | 12/2006 | Tsujii et al. ........................ 73/81 |
| 2013/0125631 | A1 | * | 5/2013 | Sadahiro ........................... 73/81 |

FOREIGN PATENT DOCUMENTS

| FR | 2619917 A1 * | 3/1989 | ............... G01N 3/42 |
| JP | 63298024 A * | 12/1988 | ............... G01N 3/42 |
| JP | 2003-166923 | 6/2003 | |

OTHER PUBLICATIONS

U.S. Appl. No. 13/238,022 to Fumihiro Takemura et al., which was filed Sep. 21, 2011.
U.S. Appl. No. 13/226,687 to Takeshi Sawa et al., which was filed Sep. 7, 2011.

* cited by examiner

*Primary Examiner* — David A Rogers
(74) *Attorney, Agent, or Firm* — Greenblum & Bernstein, P.L.C.

(57) ABSTRACT

A hardness tester includes a monitor capable of displaying a main screen and assistant screen. A first test location setter sets a coordinate point of an indentation formation location, and stores a setting condition of the set coordinate point and the surface image of a first test specimen. A second test location setter displays the surface image of the first test specimen in the assistant screen when a surface image of a second test specimen is displayed on the main screen, and, when a reference coordinate is set on the surface image of the second test specimen, determines a coordinate point of an indentation formation location based on the set reference coordinate and the setting condition of the coordinate point stored by the first test location setter.

6 Claims, 14 Drawing Sheets

CLICK LOCATION

HARDNESS TESTER WITH A USER INTERFACE FOR SETTING TEST LOCATIONS

CROSS-REFERENCE TO RELATED APPLICATIONS

The present application claims priority under 35 U.S.C. §119 of Japanese Application No. 2010-226292, filed on Oct. 6, 2010, the disclosure of which is expressly incorporated by reference herein in its entirety.

BACKGROUND OF THE INVENTION

1. Field of the Invention

The present invention relates to a hardness tester.

2. Description of Related Art

Conventionally, a hardness tester is known in which an indenter loaded with a predetermined load is pressed against a surface of a test specimen to form an indentation, and hardness of the test specimen is evaluated based on a diagonal length of the indentation and the loaded load (for example, see Japanese Patent Laid-Open Publication No. 2003-166923). In such a hardness tester, in a case where a same test is performed with respect to a plurality of test specimens, first, during a test with respect to a first test specimen, a coordinate system is set at a predetermined location on the test specimen, and a test procedure for performing a test at a predetermined point in the coordinate system is stored. Then, with respect to a subsequent test specimen, when a coordinate system is set, the stored test procedure is used to repeat the same test as that performed with respect to the first test specimen.

However, in a hardness tester, a relatively high magnification lens is usually mounted in a camera in order to improve accuracy of reading of an indentation. Therefore, it is difficult to identify which location of which test specimen is pictured in a camera image, so it is hard to set the coordinate system that has been set with respect to the first test specimen on a subsequent test specimen. Therefore, there is a problem that, when performing a same test with respect to a plurality of test specimens, the operability is poor and it is possible that an incorrect test is performed.

SUMMARY OF THE INVENTION

A feature of the present invention is to improve the operability of a hardness tester for the case where a same test is performed with respect to a plurality of test specimens.

To achieve the above feature, one aspect of the present invention is a hardness tester for forming indentation by sequentially pressing an indenter loaded with a predetermined load against surfaces of a plurality of test specimens mounted on a test specimen stage. The hardness tester includes a display, a first test location setter, and a second test location setter. The display is capable of displaying a main screen and an assistant screen. The main screen displays a surface image of a test specimen, which is among the plurality of the test specimens and which is to have an indentation formed thereon by using the indenter. The assistant screen displays an assistant image to assist a user. The first test location setter sets a test location of a first test specimen among the plurality of the test specimens. The second test location setter sets a test location of a second or subsequent test specimen among the plurality of the test specimens. The first test location setter includes a first coordinate setter, an indentation formation location setter, a setting condition storage, and an image storage. The first coordinate setter sets a reference coordinate on the surface image of the first test specimen in response to a coordinate setting operation by a user with respect to the surface image of the first test specimen in a case where the surface image of the first test specimen is displayed in the main screen. The indentation formation location setter sets a coordinate point of an indentation formation location in response to an indentation formation location setting operation by a user with respect to the surface image of the first test specimen after the reference coordinate is set by the first coordinate setter. The setting condition storage stores a setting condition of the coordinate point set by the indentation formation location setter. The image storage stores the surface image of the first test specimen displayed in the main screen. The second test location setter includes an assistant image display controller, a second coordinate setter, and an indentation formation location determiner. The assistant image display controller displays the surface image of the first test specimen as the assistant image in the assistant screen in a case where a surface image of the second or subsequent test specimen is displayed in the main screen. The second coordinate setter sets a reference coordinate on the surface image of the second or subsequent test specimen in response to a coordinate setting operation by a user with respect to the surface image of the second or subsequent test specimen displayed in the main screen. The indentation formation location determiner determines a coordinate point of an indentation formation location based on the reference coordinate set by the second coordinate setter and the setting condition of the coordinate point stored in the setting condition storage.

Another aspect of the present invention is that the above described hardness tester further includes a main image display controller, which overlappingly displays a location specified by the coordinate setting operation and a reference coordinate set by the first coordinate setter on the surface image of the first test specimen displayed in the main screen.

Another aspect of the present invention is that, in the above described hardness tester, the image storage stores the image that overlappingly displays the location specified by the coordinate setting operation and the reference coordinate set by the first coordinate setter on the surface image of the first test specimen; and the assistant image display controller displays, in the assistant screen, the image that overlappingly displays the location specified by the coordinate setting operation and the reference coordinate set by the first coordinate setter on the surface image of the first test specimen.

Another aspect of the present invention is that, in the above described hardness tester, the image storage stores a surfaces image of the second or subsequent test specimen having an indentation formed thereon.

According to the present invention, the surface image stored when an indentation is formed on the first test specimen can be displayed when an indentation is formed on the second or subsequent test specimen. Therefore, the operation to set the reference coordinate that has been set with respect to the first test specimen to the second or subsequent test specimen becomes easy to understand, and, even in the case where a same test is performed with respect to a plurality of test specimens, the test can be efficiently and correctly performed. Further, the setting condition of the coordinate point of the indentation formation location that has been set with respect to the first test specimen can be used to set the coordinate point of the indentation formation location of the second or subsequent test specimen. Therefore, even in the case where a same test is performed with respect to a plurality of test specimens, the test can be efficiently and correctly performed.

BRIEF DESCRIPTION OF THE DRAWINGS

The present invention is further described in the detailed description which follows, in reference to the noted plurality of drawings by way of non-limiting examples of exemplary embodiments of the present invention, in which like reference numerals represent similar parts throughout the several views of the drawings, and wherein.

DETAILED DESCRIPTION OF THE INVENTION

The particulars shown herein are by way of example and for purposes of illustrative discussion of the embodiments of the present invention only and are presented in the cause of providing what is believed to be the most useful and readily understood description of the principles and conceptual aspects of the present invention. In this regard, no attempt is made to show structural details of the present invention in more detail than is necessary for the fundamental understanding of the present invention, the description is taken with the drawings making apparent to those skilled in the art how the forms of the present invention may be embodied in practice.

In the following, with reference to the drawings, a hardness tester according to the present embodiment is explained in detail. In the following, a left-right direction, a front-back direction, and a height-wise direction of the hardness tester are respectively chosen as an X direction, a Y direction, and a Z direction.

Figure 1:
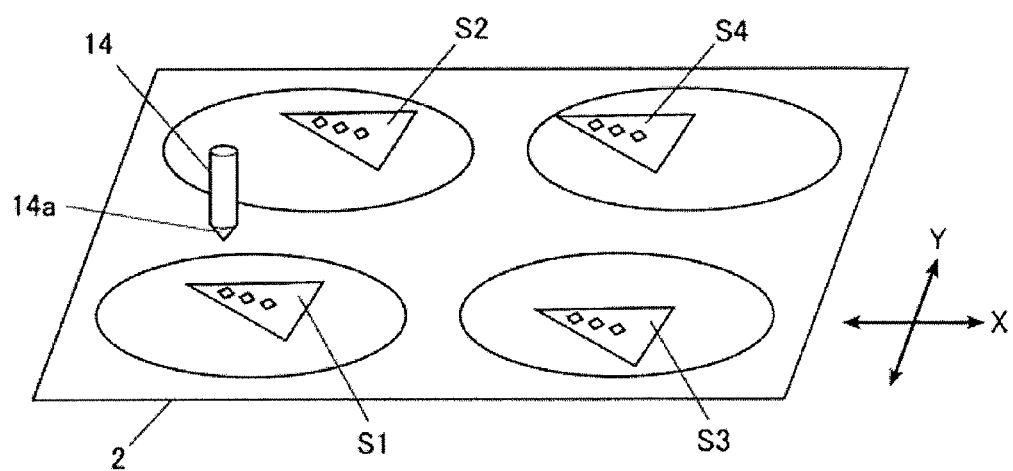
FIG. 1 is a schematic diagram illustrating a test specimen mounted on a test specimen stage.
Figure 2:
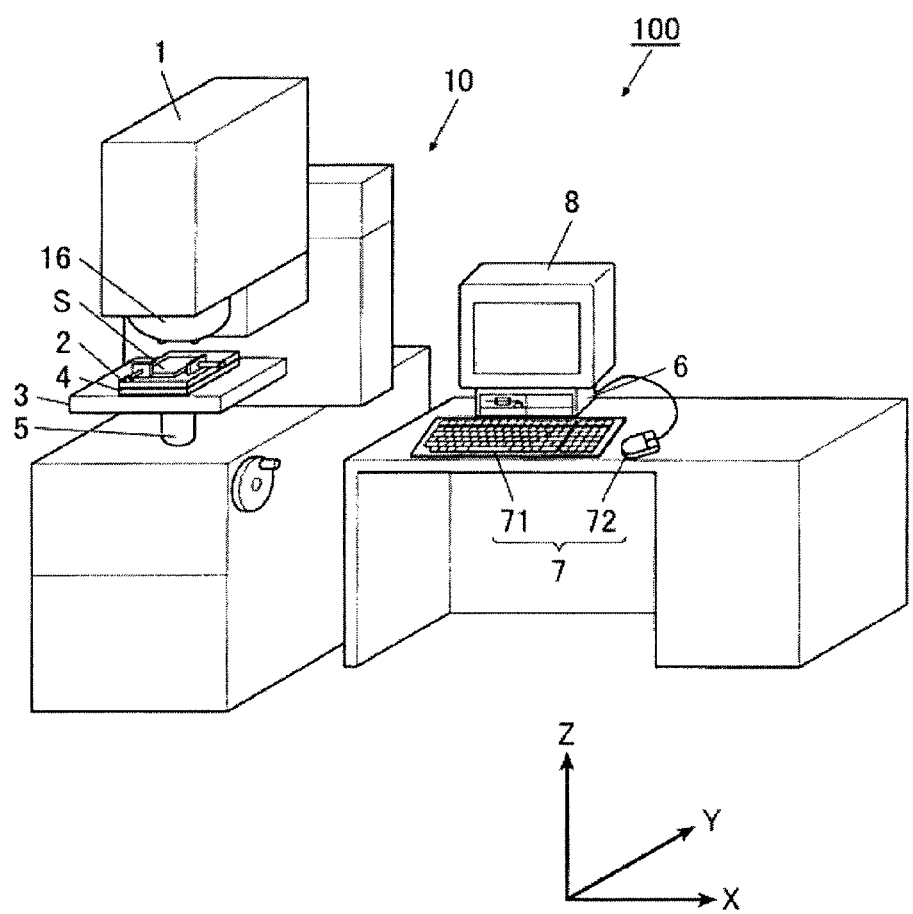
FIG. 2 is a schematic diagram illustrating an overall configuration of a hardness tester according to the present invention.

A hardness tester 100 according to the present embodiment is, for example, as illustrated in FIG. 1, a hardness tester capable of sequentially forming indentations with respect to a plurality of test specimens S (S1-S4) of a same shape mounted on a test specimen stage 2. In the hardness tester 100, a "first test location setting process" setting a test location with respect to a first test specimen, and a "second test location setting process" setting a test location with respect to a second or subsequent test specimen, are executed. In the first test location setting process, a test location is set with respect to the first test specimen, and a setting procedure performed at this time is stored. Further, in the first test location setting process, by repeating the same test using the setting procedure stored during the first test location setting process, a test location is set with respect to the second or subsequent test specimen. This allows the hardness tester 100 to sequentially perform the same test with respect to the plurality of the test specimens S of the same shape.

Specifically, the hardness tester 100 is, for example, a micro-Vickers hardness tester, and, as FIGS. 2-6 illustrate, includes a tester body 10, a controller 6, an operator 7, a monitor 8, and the like.

Figure 3:
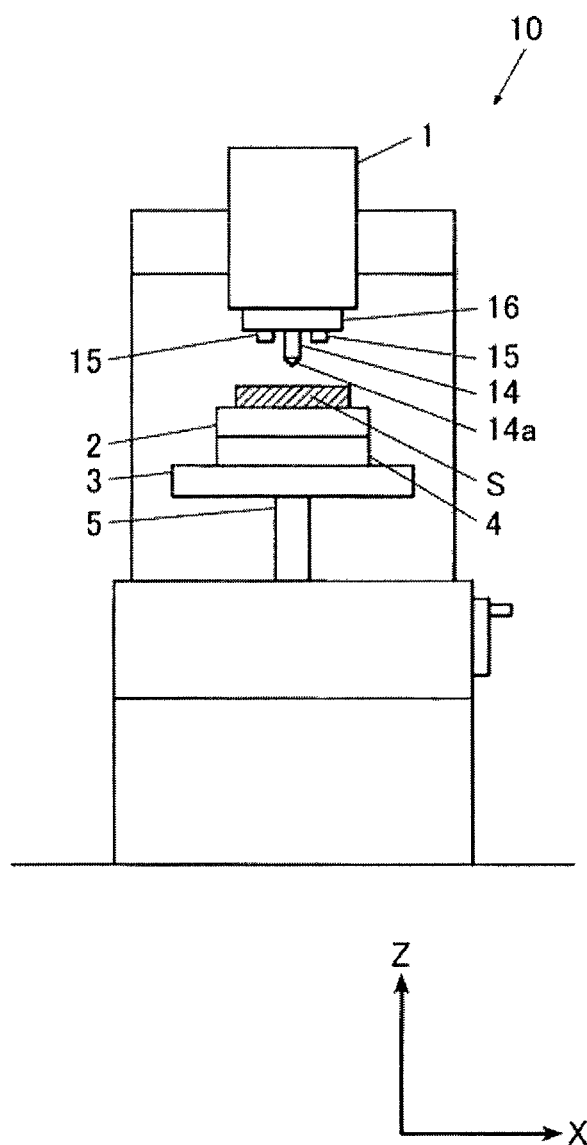
FIG. 3 is a schematic diagram illustrating a tester body of the hardness tester illustrated in FIG. 1.
Figure 4:
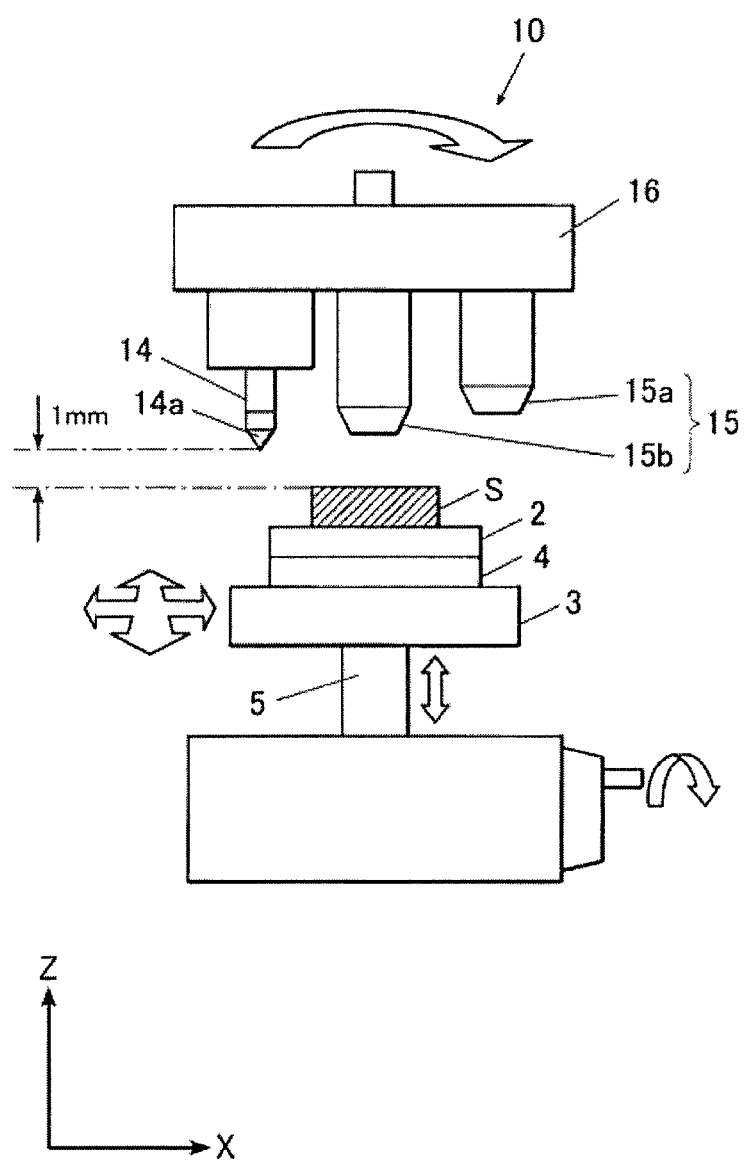
FIG. 4 is a schematic diagram illustrating a configuration of a key section of the hardness tester illustrated in FIG. 1.

The tester body 10, for example, as FIGS. 3 and 4 illustrate, includes a hardness measurer 1 performing hardness measurement with respect to the test specimens S, a test specimen stage 2 mounting the test specimens S thereon, an XY stage 3 moving the test specimen stage 2, an AF (Z) stage 4 for focusing on a surface of a test specimen S, a lifting mechanism 5 moving the test specimen stage 2 (the XY stage 3, and the AF (Z) stage 4) up and down, and the like.

Figure 5:
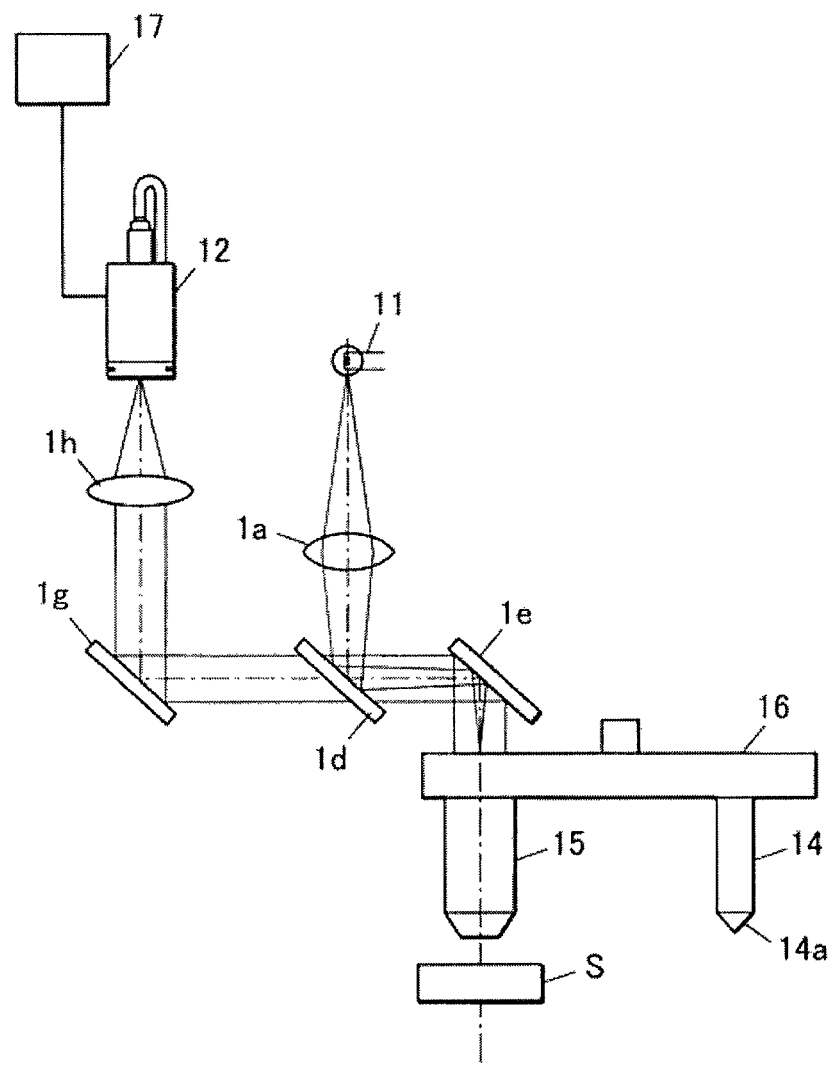
FIG. 5 is a schematic diagram illustrating a hardness measurer of the hardness tester illustrated in FIG. 1.

As FIG. 5 illustrates, the hardness measurer 1 includes, for example, a lighting device 11 lighting a surface of a test specimen S, a CCD (Charge Coupled Device) camera 12 capturing an image of the surface of the test specimen S, an turret 16, and the like, the turret 16 including an indenter shaft 14, which has an indenter 14a, and an objective lens 15, and being capable of switching between the indenter shaft 14 and the objective lens 15 by rotation.

The lighting device 11 lights the surface of the test specimens S by radiating light. The light radiated from the lighting device 11 arrives at the surface of the test specimens S via a lens 1a, a half mirror 1d, a mirror 1e, and the objective lens 15.

The CCD camera 12 captures an image of a surface of a test specimen S in its turn to have an indentation formed thereon by the indenter 14a, the test specimen S being among the plurality of the test specimens S mounted on the test specimen stage 2. Based on reflected light input from the surface of the test specimen S via the objective lens 15, the mirror 1e, the half mirror 1d, a mirror 1g, and a lens 1h, the CCD camera 12 captures images of the surface of the test specimen S and the indentation formed on the surface of the test specimen S by the indenter 14a, obtains image data, and outputs the data to the controller 6 via a frame grabber 17, which is capable of simultaneously accumulating and storing image data of a plurality of frames.

The indenter shaft 14 is moved toward the test specimen S mounted on the test specimen stage 2 by a loading mechanism (not shown in the drawings), which is driven in response to a control signal output by the controller 6. The indenter 14a, which is provided at an apical portion of the indenter shaft 14, is pressed against the surface of the test specimen S with a predetermined test force.

A plurality of objective lenses 15, which are respectively equipped with condenser lenses 15a and 15b of different magnifications, are held on a lower surface of the turret 16, and are positioned above the test specimen S by the rotation of the turret 16, thereby allowing light radiated from the lighting device 11 to uniformly irradiate the surface of the test specimen S.

The turret 16 is configured to have the indenter shaft 14 and the plurality of the objective lenses 15 attached on its lower surface, and be capable of switching any one of the indenter shaft 14 and the plurality of the objective lenses 15 to a position above the test specimen S by rotating around an axis in the Z axis direction. In other words, by lowering the indenter shaft in a state in which the indenter shaft 14 is positioned above the test specimen S, an indentation is formed on the surface of the test specimen S; and, by positioning the objective lens 15 above the test specimen S, the formed indentation can be observed.

In the present embodiment, the test specimen stage 2 has the plurality of the test specimens S of a same shape mounted on an upper surface thereof. The XY stage 3 is driven by a driving mechanism (not shown in the drawings), which is driven in response to a control signal output by the controller 6, and moves the test specimen stage 2 in a direction (the X axis direction and the Y axis direction) perpendicular to the movement direction (the Z axis direction) of the indenter 14a. That is, when a test with respect to one test specimen is completed, the XY stage 3 moves the test specimen stage 2 in the X axis direction and the Y axis direction so that a next test specimen is in a position facing the indenter 14a. The AF (Z) stage 4 is driven in response to a control signal output by the controller 6, and, based on the image data captured by the CCD camera 12, finely moves the test specimen stage 2 up and down to focus on the surface of the test specimen S. The lifting mechanism 5 is driven in response to a control signal output by the controller 6, and changes a relative distance between the test specimen stage 2 and the objective lens 15 by moving the test specimen stage 2 (the XY stage 3 and the AF (Z) stage 4) in the up-down direction.

The operator 7 includes a keyboard 71, a mouse 72, and the like, and allows a user to execute an input operation when performing a hardness test. When a predetermined input operation is performed by the operator 7, a predetermined operation signal corresponding to the input operation is output to the controller 6. Specifically, the operator 7 is used when a user performs a "coordinate setting operation" and an "indentation formation location setting operation" with respect to a surface image of the test specimen S displayed in a main screen A1 (to be described later) on the monitor 8.

The coordinate setting operation is an operation in which a user specifies a location that sets a reference coordinate for determining an indentation formation location with respect to a surface image of the test specimen S displayed in the main screen A1 on the monitor 8 in the first test location setting process and the second test location setting process. The indentation formation location setting operation is an operation in which a user specifies an indentation formation location with respect to the surface image of the test specimen S after the reference coordinate is set on the surface image of the test specimen S displayed in the main screen A1 on the monitor 8 in the first test location setting process.

Further, the operator 7 is used by a user to set various conditions when a hardness test is performed using the hardness tester 100. Here, the setting for various conditions means, for example, setting for test conditions (values of a material property of the test specimen S, a test force (N) loaded on the test specimen S by the indenter 14a, magnification of the objective lens 15, and the like), a test starting point, numbers of rows and columns, a pitch, and the like.

The monitor 8 includes a display device, for example, such as an LCD (Liquid Crystal Display) or the like, and displays a setting condition of a hardness test input by using the operator 7, a result of the hardness test, a surface image of the test specimen S captured by the CCD camera 12, an image of an indentation formed on the surface of the test specimen S, and the like. This allows the monitor 8 to act as a display.

Here, a display screen displayed on the monitor 8 is explained with reference to FIGS. 7 and 8.

Figure 7:
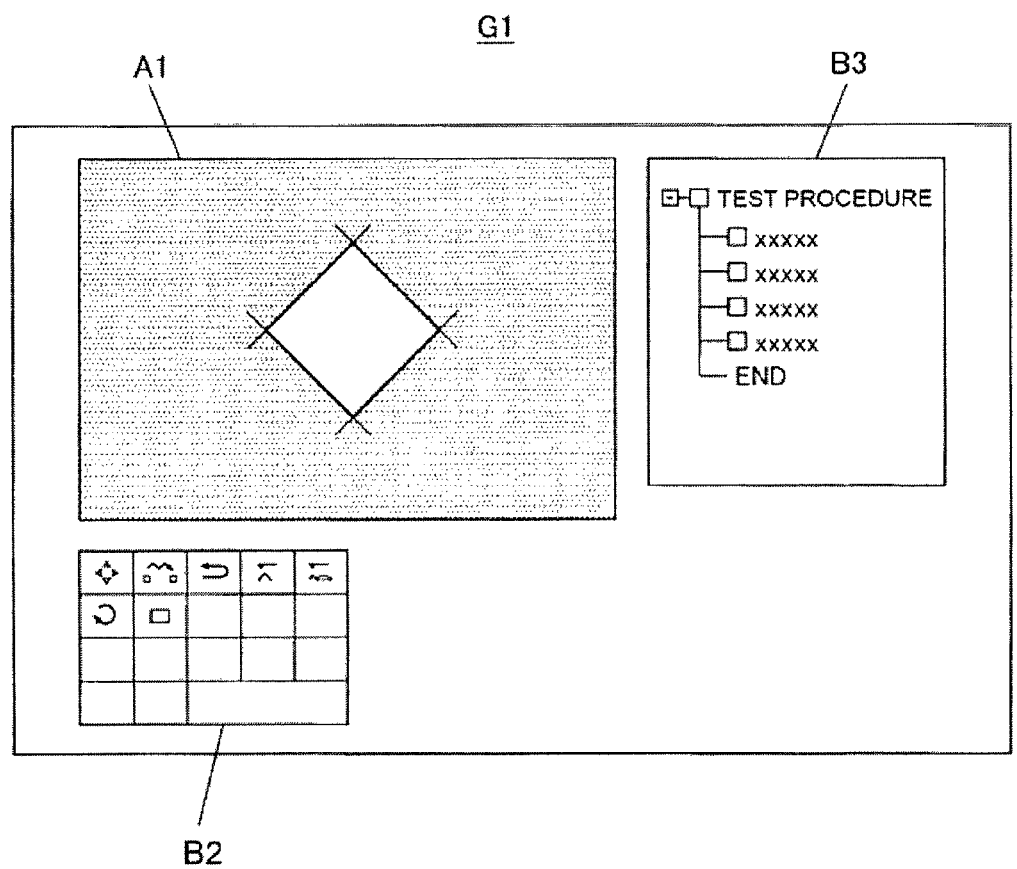
FIG. 7 is an example of a display screen displayed on a monitor when a test is performed with respect to a first test specimen.

FIG. 7 is an example of a display screen G1 displayed on the monitor 8 when an indentation is formed with respect to a first test specimen S1 (when the first test location setting process is performed). The display screen G1 includes the main screen A1, a toolbox B2, a test procedure display area B3, and the like. In the display screen G1, a surface image of the first test specimen S1 captured by the CCD camera 12 is displayed in the main screen A1. A high magnification lens is mounted in the CCD camera 12. Therefore, an enlarged image capturing a portion of a test specimen S is displayed in the main screen A1. In the toolbox B2, various tools for performing various operations such as the coordinate setting operation, the indentation formation location setting operation, and the like, are listed. When performing a coordinate setting operation, a user can select an appropriate tool and can specify any point in the main screen A1 by clicking on the main screen A1. When performing an indentation formation location setting operation, a user can select an appropriate tool and can specify any point in the main screen A1 as an indentation formation location by clicking on the main screen A1. In the test procedure display area B3, a test procedure to be performed with respect to the first test specimen S1 is displayed.

Figure 8:
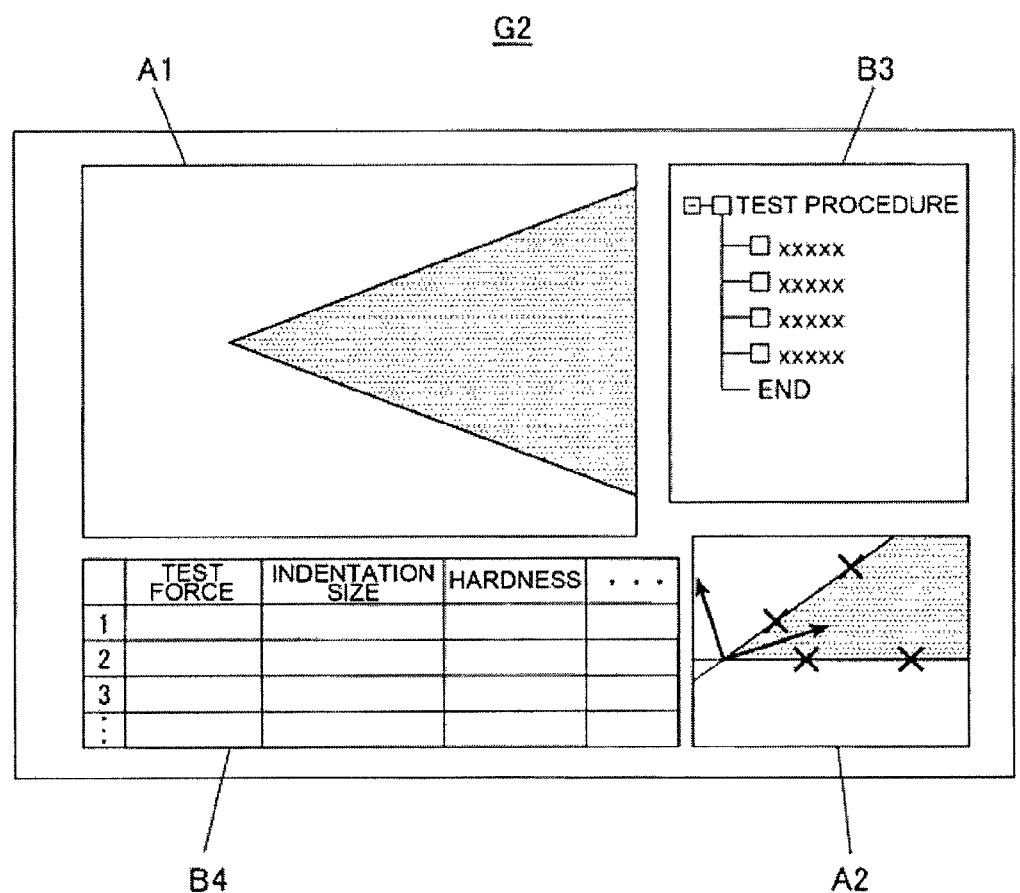
FIG. 8 is an example of a display screen displayed on the monitor when a test is performed with respect to a second or subsequent test specimen.

FIG. 8 is an example of a display screen G2 displayed on the monitor 8 when an indentation is formed with respect to the second or subsequent test specimen (when the second test location setting process is performed). The display screen G2 includes the main screen A1, an assistant screen A2, the test procedure display area B3, a test result display area B4, and the like. In the display screen G2, a surface image of the second or subsequent test specimen (here, the second test specimen S2) captured by the CCD camera 12 is displayed in the main screen A1. The surface image of the first test specimen S1 is displayed in the assistant screen A2 as an assistant image. The assistant screen A2 is a screen displayed on the monitor 8 and used when the second test location setting process is performed, and displays the surface image of the first test specimen S1 in the case where the surface image of the second or subsequent test specimen S is displayed in the main screen A1. In the test procedure display area B3, a test procedure prepared based on the indentation formation of the first test specimen S1 is listed. In the test result display area B4, test results such as a test force, a size of an indentation, hardness, and the like are displayed.

Figure 6:
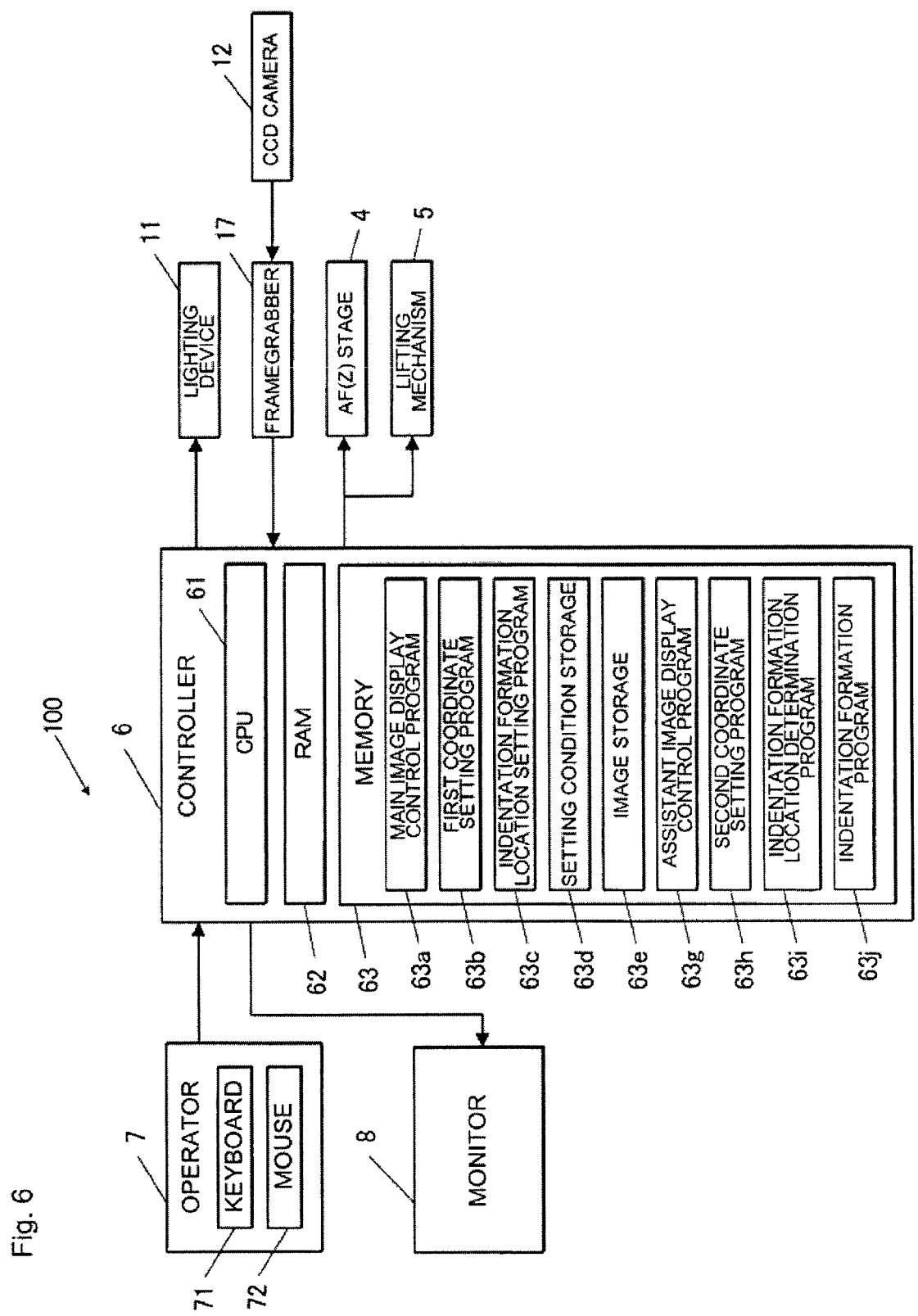
FIG. 6 is a block diagram illustrating a control configuration of the hardness tester illustrated in FIG. 1.

The controller 6, as FIG. 6 illustrates, includes a CPU (Central Processing Unit) 61, a RAM (Random Access Memory) 62, a memory 63, and the like, and performs operation control and the like for performing a predetermined hardness test by executing a predetermined program stored in the memory 63.

The CPU 61 reads out a processing program stored in the memory 63, deploys the program in the RAM 62 and executes the program, and thereby, performs control of the entire hardness tester 100.

The RAM 62 deploys, in a program storage area within the RAM 62, a processing program and the like executed by the CPU 61, and stores, in a data storage area, input data, a processing result generated when the processing program is executed, and the like.

The memory 63 includes a recording medium (not shown in the drawings) storing, for example, a program, data, and the like. The recording medium is composed of a semiconductor memory and the like. The memory 63 stores various data, various processing programs, data processed by executing the programs, and the like, for causing the CPU 61 to control the entire hardness tester 100.

More specifically, the memory 63 stores, for example, a main image display control program 63a, a first coordinate setting program 63b, an indentation formation location setting program 63c, a setting condition storage 63d, an image storage 63e, an assistant image display control program 63g, a second coordinate setting program 63h, an indentation formation location determination program 63i, an indentation formation program 63j, and the like.

The main image display control program 63a is a program that causes the CPU 61 to display a surface image of a test specimen captured by the CCD camera 12 in the main screen A1. Here, the CPU 61 displays the display screen G1 on the monitor 8 in the case where a test with respect to the first test specimen S1 is performed (the case where the first test location setting process is performed). The CPU 61 displays the surface image of the first test specimen S1 in the main screen A1 when an image of the first test specimen S1 is captured. At this time, the CPU 61 stores the surface image of the test specimen S1 as an initial image in the image storage 63e. Further, the CPU 61 displays the display screen G2 on the monitor 8 in the case where a test with respect to the second or subsequent test specimen S is performed (the case where the second test location setting process is performed). The CPU 61 displays a surface image of the second or subsequent specimen S in the main screen A1 when an image of the second or subsequent test specimen S is captured.

Further, the main image display control program 63a is a program that causes the CPU 61 to overlappingly display a location specified by the coordinate setting operation and a reference coordinate set by executing the first coordinate setting program 63b (to be described in detail later) on the surface image of the first test specimen S1 displayed in the main screen A1. Specifically, with respect to the surface image (initial image) of the first test specimen S1 displayed in the main screen A1, in the case where the coordinate setting operation is performed and in the case where the reference coordinate is set, the CPU 61 overlappingly displays the location specified by the coordinate setting operation and the set reference coordinate on the surface image of the test specimen S1 in a manner that the location specified by the coordinate setting operation and the set reference coordinate are identifiable. At this time, the CPU 61 stores, in the image storage 63e, the image that overlappingly displays the location specified by the coordinate setting operation and the reference coordinate on the initial image of the test specimen S1.

By executing such a main image display control program 63a, the CPU 61 acts as a main image display controller.

The first coordinate setting program 63b is a program that causes the CPU 61 to set a reference coordinate on the surface image of the first test specimen S1 in response to a coordinate setting operation by a user with respect to the surface image of the first test specimen S1, in the case where the surface image of the first test specimen S1 is displayed in the main screen A1. Here, as an example, a case is explained in which, as FIGS. 9(a)-9(d) illustrate, a corner of a triangular test specimen S1 is displayed in the main screen A1; a reference coordinate is set in a manner that an X axis is set on a bisector of the corner of the test specimen S1 and a Y axis is set as originating from a vertex of the corner of the test specimen S1 and perpendicular to the X axis; and indentations are formed at a plurality of points on the X axis.

Figure 9:
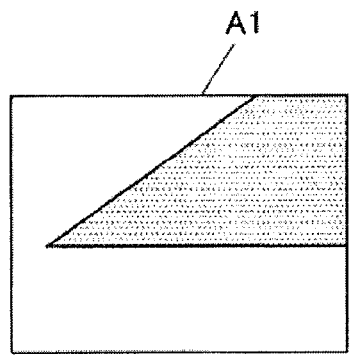
FIG. 9 illustrates diagrams for explaining transition of a main image.
Figure 9:
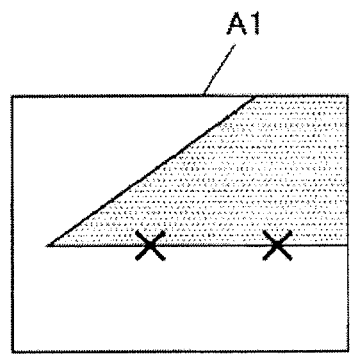
Figure 9:
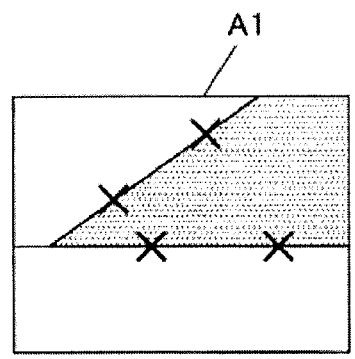
Figure 9:
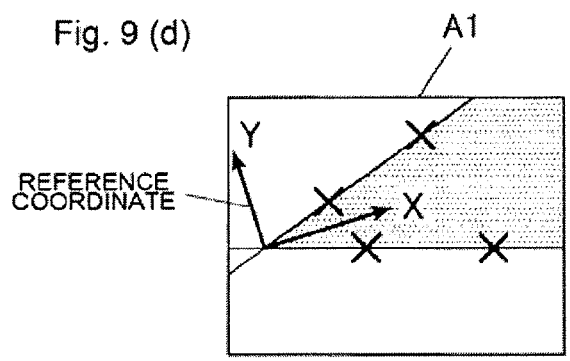

When the surface image of the first test specimen S1 is displayed in the main screen A1 as illustrated in FIG. 9(a), a user clicks two points on the displayed image using a predetermined tool in the toolbox B2 as the coordinate setting operation, as illustrated in FIG. 9(b). When this is done, the CPU 61 obtains one side (one side of the test specimen S1) based on the clicked two points. Further, as the coordinate setting operation, a user clicks two points different from the above two points on the displayed image, as illustrated in FIG. 9(c). When this is done, the CPU 61 obtains another side (another side of the test specimen S1) based on the clicked two points. At this time, the CPU 61 overlappingly displays the locations specified by the coordinate setting operation on the surface image of the test specimen S1 using the main image display control program 63a, and stores the image in the image storage 63e.

Next, as illustrated in FIG. 9(d), the CPU 61 obtains a bisector between the obtained two sides, sets the X axis on the bisector, and sets the Y axis as originating from an intersection point (a vertex of the test specimen S1) of the obtained two sides and perpendicular to the X axis. At this time, the CPU 61 overlappingly displays the set X axis and Y axis (the reference coordinate) on the surface image of the test specimen S1 using the main image display control program 63a, and stores the image in the image storage 63e.

By executing such a first coordinate setting program 63b, the CPU 61 acts as a first coordinate setter.

The indentation formation location setting program 63c is a program that causes the CPU 61 to set a coordinate point of an indentation formation location in response to an indentation formation location setting operation by a user with respect to the surface image of the first test specimen S1, after setting the reference coordinate by executing the first coordinate setting program 63b. When the reference coordinate is set with respect to the surface image of the first test specimen S1 displayed in the main screen A1, a user clicks an arbitrary location on the displayed image using a predetermined tool in the toolbox B2 as the indentation formation location setting operation. The CPU 61 calculates a coordinate point of the clicked location based on the reference coordinate, and sets this coordinate point as an indentation formation location. When the coordinate point of the indentation formation location is set by executing the indentation formation location setting program 63c, the CPU 61 executes the indentation formation program 63j (to be described later) to form an indentation on the first test specimen S1. By executing such an indentation formation location setting program 63c, the CPU 61 acts as an indentation formation location setter.

The setting condition storage 63d stores the setting condition of the coordinate point set by the indentation formation location setting program 63c. The setting condition is a condition that indicates for what kind of shape an indentation is formed and how such an indentation is formed. For example, here, a setting condition indicating that a plurality of indentations are formed on the bisector of the corner at a predetermined spacing (coordinate points are set on the bisector of the corner) is stored.

The image storage 63e, as an image storage, stores various images displayed in the main screen A1. Specifically, the image storage 63e stores the surface image (initial image) of the first test specimen S1. Further, the image storage 63e stores the image that overlappingly displays the location specified by the coordinate setting operation and the set reference coordinate on the initial image of the test specimen S1. Further, the image storage 63e stores the surface image of the first test specimen S1 having an indentation formed thereon. Further, the image storage 63e can also store a surface image of the second or subsequent test specimen S having an indentation formed thereon.

Figure 10:
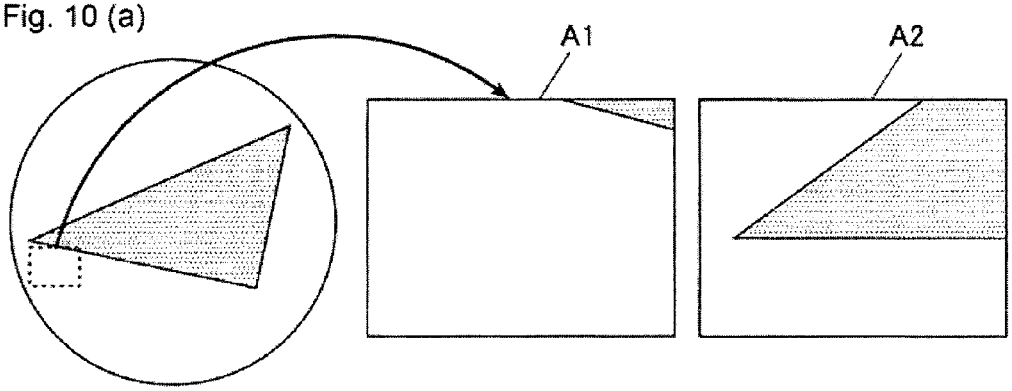
FIG. 10 illustrates diagrams for explaining transition of a main image and an assistant image.
Figure 10:
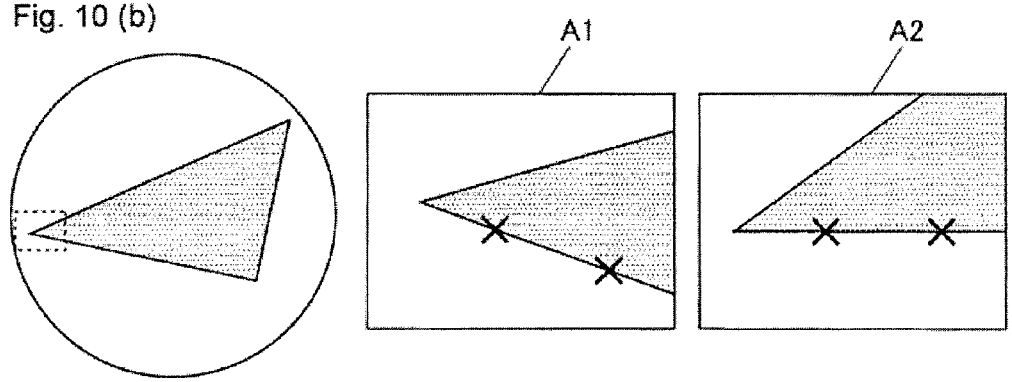
Figure 10:
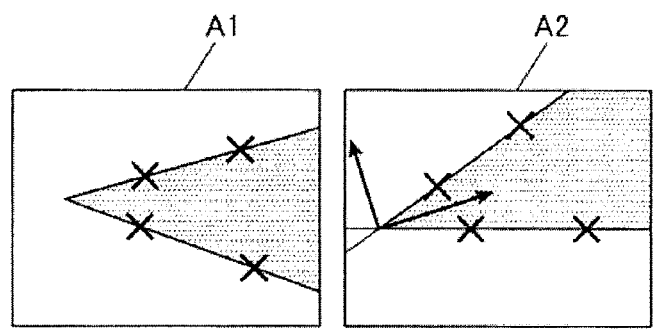

The assistant image display control program 63g is a program that causes the CPU 61 to display the surface image of the first test specimen S1 in the assistant screen A2 as an assistant image, in the case where a surface image of the second or subsequent test specimen S is displayed in the main screen A1. As describe above, the CPU 61 displays the display screen G2 on the monitor 8 in the case where a test with respect to the second or subsequent test specimen S is performed (the case where the second test location setting process is performed). The CPU 61 displays the surface image of the first test specimen S1 stored in the image storage 63e in the assistant screen A2 as an assistant image, in the case where the surface image of the second or subsequent test specimen S is displayed in the main screen A1 of the display screen G2. Therefore, even when the surface image of the second test specimen S2 displayed in the main screen A1 does not display a desired location, for example, as illustrated in FIG. 10(*a*), the user can adjust the location of the test specimen S2 so that an image nearly identical to that displayed in the assistant screen A2 is displayed as illustrated in FIG. 10(*b*). That is, an enlarged image capturing a portion of the test specimen S2 is displayed in the main screen A1. Therefore, location identification is difficult. However, the image displayed in the assistant screen A2 can be used as a reference. Therefore, the location of the test specimen S2 can be easily identified and location adjustment can be easily performed.

Further, the CPU 61 changes the assistant image according to the image displayed in the main screen A1. For example, the CPU 61 displays the initial image of the first test specimen S1 in the assistant screen A2 immediately after the surface image of the second test specimen S2 is displayed in the main screen A1. However, when a user performs a coordinate setting operation with respect to the surface image of the second test specimen S2, the CPU 61 displays in the assistant screen A2 an image overlappingly displaying the location specified by the coordinate setting operation by the user, an image overlappingly displaying the reference coordinate, and the like, on the initial image of the test specimen S 1. Therefore, the user can confirm the location specified by the coordinate setting operation, the set reference coordinate, and the like, using the assistant screen A2.

By executing such an assistant image display control program 63g, the CPU 61 acts as an assistant image display controller.

The second coordinate setting program 63h is a program that causes the CPU 61 to set a reference coordinate on the surface image of the second or subsequent test specimen S in response to a coordinate setting operation by a user with respect to the surface image of the second or subsequent test specimen S displayed in the main screen A1. When the surface image of the second or subsequent test specimen S is displayed in the main screen A1, a user clicks two points in the main screen A1 using a predetermined tool in the toolbox B2 as a coordinate setting operation, as illustrated in FIG. 10(*b*). When this is done, the CPU 61 obtains one side (one side of the test specimen S2) based on the clicked two points. Further, as the coordinate setting operation, the user clicks other two points in the main screen A1 using a predetermined tool in the toolbox B2, as illustrated in FIG. 10(*c*). When this is done, the CPU 61 obtains another side (another side of the test specimen S2) based on the clicked two points. At this time, as illustrated in FIGS. 10(*b*) and 10(*c*), the surface image of the first test specimen S1 is displayed in the assistant screen A2. Therefore, the user can easily perform the coordinate setting operation.

Next, with reference to the setting condition stored in the setting condition storage 63d, the CPU 61 sets a reference coordinate on the surface image of the second or subsequent test specimen S when the CPU has determined that a coordinate setting operation is being performed in a nearly identical pattern as that for the first test specimen S1. For example, here, the CPU 61 determines whether a coordinate setting operation specifying a corner (specifying two sides) has been performed, and, in the case where the operation specifying a corner has been performed, the CPU 61 sets the X axis on the bisector of the two sides, and sets the Y axis as originating from the intersection point of the two sides and perpendicular to the X axis. Thus, for example, even when an angle of the corner of the test specimen S2 is not exactly the same as an angle of the corner of the test specimen S1, in a similar way, the bisector of the two sides of the angle is obtained to set the reference coordinate. Thus, the reference coordinate is set also with respect to the second test specimen S2 at a similar location as that for the first test specimen S1.

By executing such a second coordinate setting program 63h, the CPU 61 acts as a second coordinate setter.

The indentation formation location determination program 63i is a program that causes the CPU 61 to determine a coordinate point of an indentation formation location based on the reference coordinate set by the second coordinate setting program 63h and the setting condition of the coordinate point stored in the setting condition storage 63d. Specifically, with reference to the setting condition stored in the setting condition storage 63d, the CPU 61 determines a coordinate point so as to perform indentation formation with respect to the second or subsequent test specimen S at the same coordinate point as the indentation formation coordinate point set with respect to the first test specimen S1. By executing such an indentation formation location determination program 63i, the CPU 61 acts as an indentation formation location determiner.

The indentation formation program 63j is a program that causes the CPU 61 to form an indentation on a test specimen S using the indenter 14a. Specifically, the CPU 61 forms an indentation with respect to the first test specimen 51 in the case where a coordinate point of an indentation formation location is set by executing the indentation formation location setting program 63c. Further, the CPU 61 forms an indentation at an indentation formation location using the indenter 14a with respect to the second or subsequent test specimen S in the case where the coordinate point of the indentation formation location is determined by executing the indentation formation location determination program 63i. At this time, the CPU 61 stores the surface image of the test specimen S having the indentation formed thereon in the image storage 63e. By executing such an indentation formation program 63j, the CPU 61 acts as an indentation former.

The first coordinate setting program 63b, the indentation formation location setting program 63c, the setting condition storage 63d, the image storage 63e, and the like, constitute the first test location setter that sets the test location of the first test specimen S1 among the plurality of the test specimens S. The assistant image display control program 63g, the second coordinate setting program 63h, the indentation formation location determination program 63i, and the like, constitute the second test location setter that sets the test location of the second or subsequent test specimen among the plurality of the test specimens S.

Figure 11:
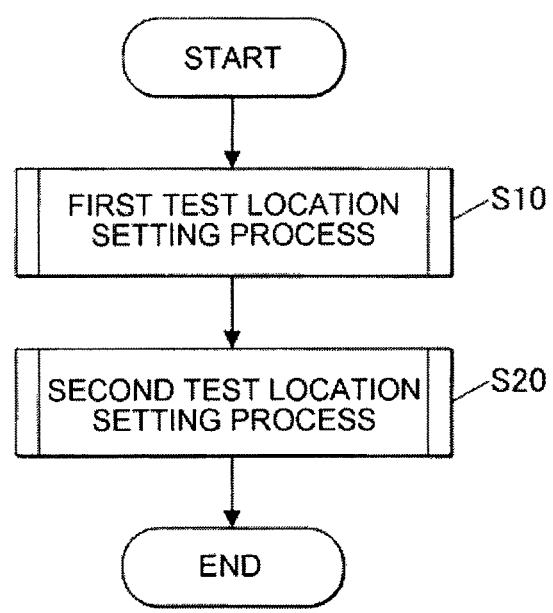
FIG. 11 is a flowchart for explaining a measurement process using the hardness tester illustrated in FIG. 1.
Figure 12:
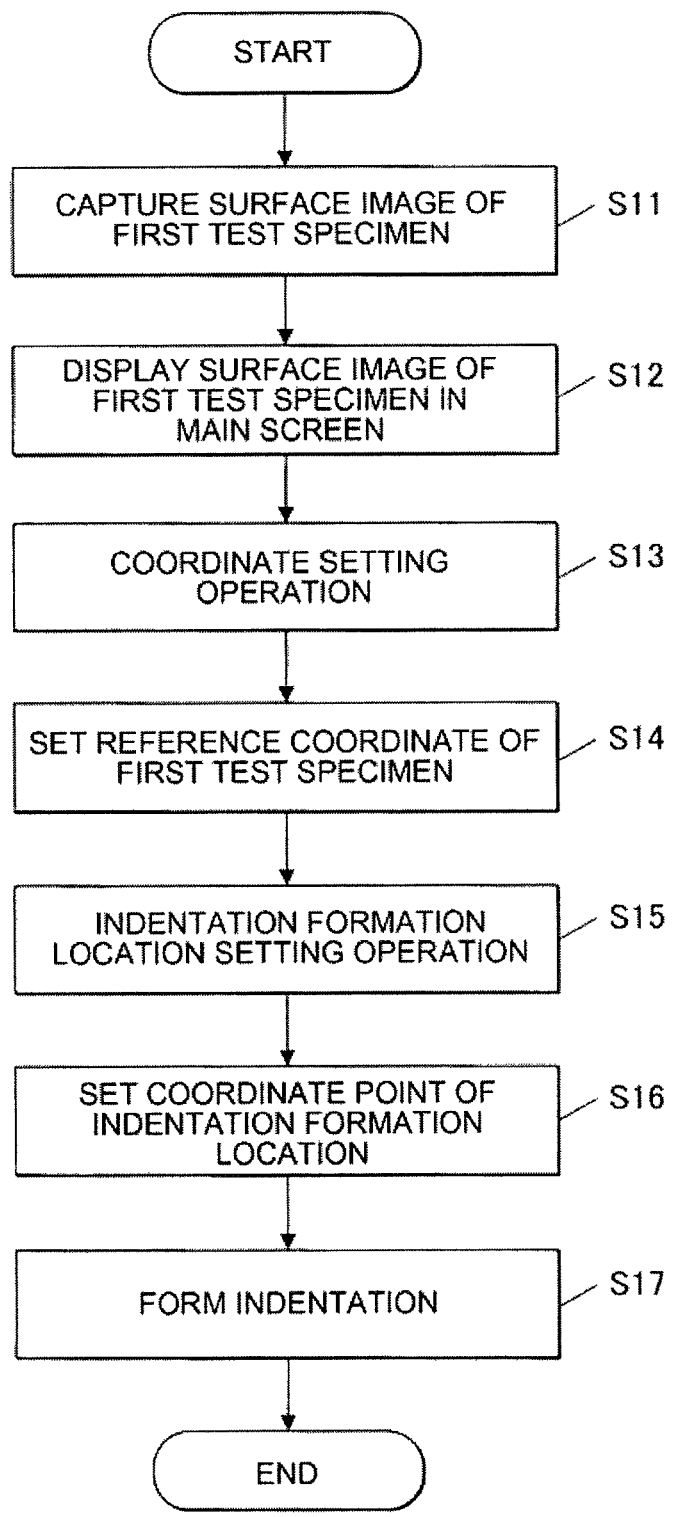
FIG. 12 is a flowchart illustrating a first test location setting process in FIG. 11.
Figure 13:
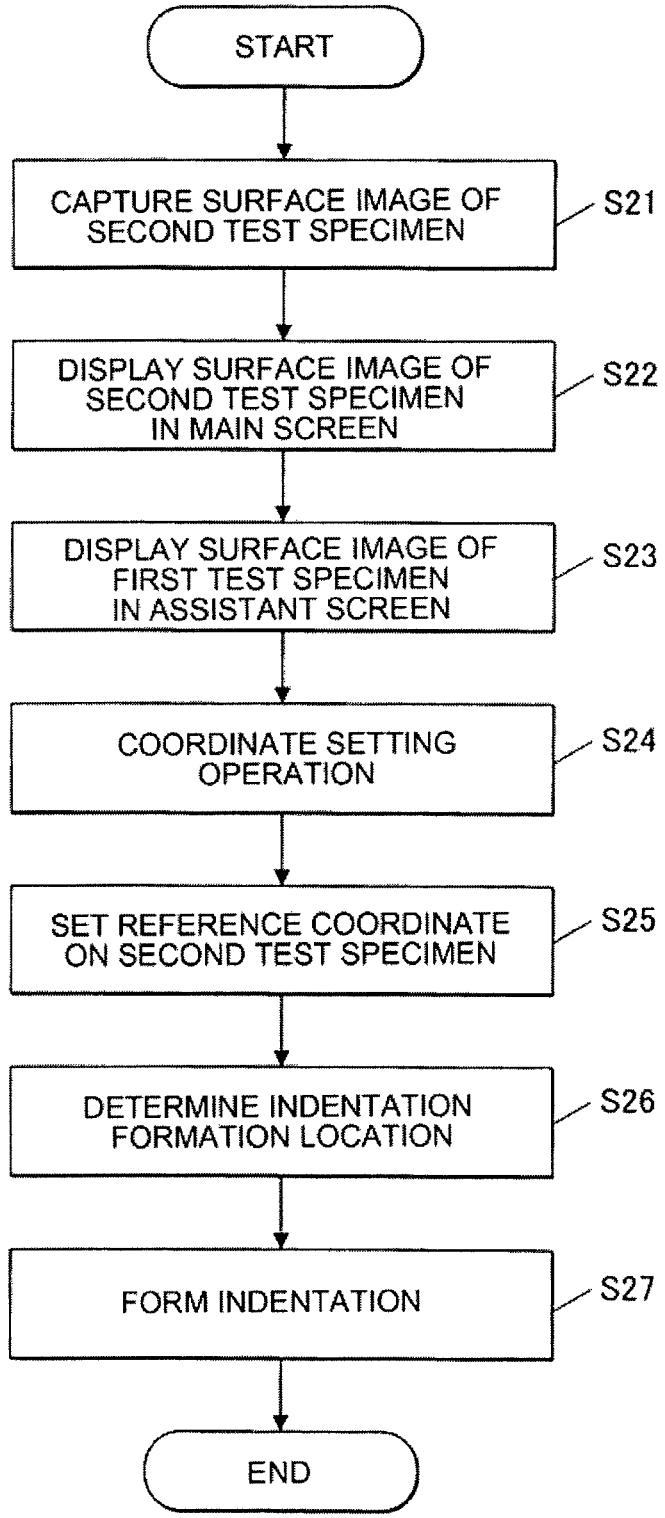
FIG. 13 is a flowchart illustrating a second test location setting process in FIG. 11.

Next, a measurement process of the hardness tester 100 is explained using flowcharts illustrated in FIGS. 11-13. As illustrated in FIG. 11, the measurement process of the hardness tester 100 includes a first test location setting process (step S10) setting a test location with respect to the first test specimen S1, and a second test location setting process (step S20) setting a test location with respect to the second or subsequent test specimen S.

FIG. 12 is a flowchart illustrating the first test location setting process. First, at a step S11, the CPU 61 captures a surface image of the first test specimen S1 using the CCD camera 12. Next, at a step S12, the CPU 61 displays the surface image of the first test specimen S1 in the main screen A1 on the monitor 8. The surface image (initial image) of the test specimen S1 is stored in the image storage 63e. Next, at a step S13, a user performs the coordinate setting operation with respect to the surface image of the first test specimen 51. The location specified by the coordinate setting operation is overlappingly displayed on the surface image of the test specimen S1, and this image is stored in the image storage 63e. Next, at a step S14, the CPU 61 sets a reference coordinate on the surface image of the first test specimen S1. The set reference coordinate is overlappingly displayed on the surface image of the test specimen S1, and this image is stored in the image storage 63e. Next, at a step S15, the user performs the indentation formation location setting operation with respect to the surface image of the first test specimen S1. Next, at a step S16, the CPU 61 sets a coordinate point of an indentation formation location using the set reference coordinate. Next, at a step S17, the CPU 61 forms an indentation at the set coordinate point. The surface image having the indentation formed on the surface is stored in the image storage 63e.

FIG. 13 is a flowchart illustrating the second test location setting process. First, at a step S21, the CPU 61 captures a surface image of the second test specimen S2 using the CCD camera 12. Next, at a step S22, the CPU 61 displays the surface image of the second test specimen S2 in the main screen A1 on the monitor 8. Next, at a step S23, the CPU 61 displays the surface image of the first test specimen S1 in the assistant screen A2 on the monitor 8. Next, at a step S24, the user performs the coordinate setting operation with respect to the surface image of the second test specimen S2. Next, at the step S24, the CPU 61 sets a reference coordinate on the surface image of the second test specimen S2. Next, at a step S25, the CPU 61 determines an indentation formation location. Next, at a step S26, the CPU 61 forms an indentation at the set coordinate point. The surface image having the indentation formed on the surface is stored in the image storage 63e.

The same process as the above steps S21-S26 is performed also with respect to a following subsequent test specimen.

As described above, according to the hardness tester 100 of the present embodiment, the surface image stored when an indentation is formed on the first test specimen S1 can be displayed in the assistant screen A2 when an indentation is formed on the second or subsequent test specimen S2-S4. Therefore, the operation to set the reference coordinate that been set with respect to the first test specimen S1 to the second or subsequent test specimen S2-S4 becomes easy to understand, and, even when a same test is performed with respect to a plurality of test specimens, the test can be efficiently and correctly performed. Further, the setting condition of the coordinate point of the indentation formation location that has been set during the test with respect to the first test specimen can be used to set the coordinate point of the indentation formation location of the second or subsequent test specimen S2-S4. Therefore, even when a same test is performed with respect to a plurality of test specimens, the test can be efficiently and correctly performed.

Further, according to the hardness tester 100 of the present embodiment, the location specified by the coordinate setting operation and the set reference coordinate are overlappingly displayed on the surface image of the first test specimen S1 displayed in the main screen A1. Therefore, at the first test location setting process (S10), a user can confirm his/her own operation. Therefore, a good operability can be achieved.

Further, according to the hardness tester 100 of the present embodiment, in the assistant screen A2, the image is displayed that overlappingly displays the location specified by the coordinate setting operation and the set reference coordinate on the surface image of the first test specimen S1. Therefore, at the second test location setting operation (S20), the location specified by the coordinate setting operation and the set reference coordinate can be confirmed using the assistant screen A2. Therefore, a good operability can be achieved.

Further, according to the hardness tester 100 of the present embodiment, the surface image of the second or subsequent test specimen S having an indentation formed thereon is stored in the image storage 63e. Therefore, a user can also display at will an image of other than the first test specimen S1 in the assistant screen A2, and thus, usability can be improved.

The above embodiment exemplified a case where a same test is performed with respect to a plurality of test specimens of a same shape. However, the present process is also applicable to a case where the test specimens are not necessarily of a same shape. For example, it is also possible that test specimens have similar configurations at indentation formations locations, but, other than that, have different shapes. Further, it is also possible to use a stitched image as an image displayed in the main screen. Further, it is also possible to perform the same process even with respect to a configuration in which a low magnification lens is mounted.

Figure 14:
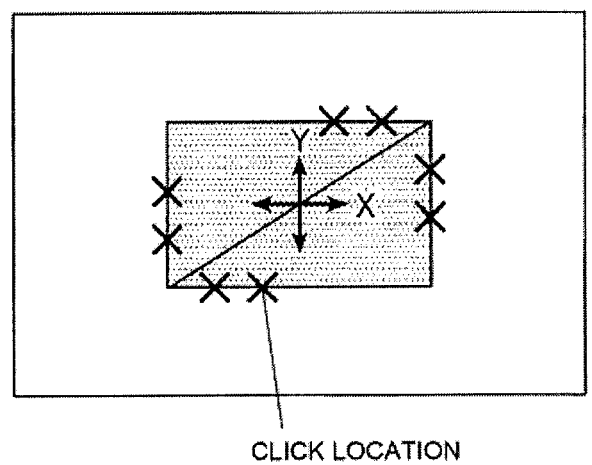
FIG. 14 is a diagram illustrating an example of variation of a test specimen.

Further, in the above embodiment, a configuration is explained with an example in which the X axis is set on a bisector of a corner of a test specimen and the Y axis is set as originating from a vertex of the test specimen and perpendicular to the X axis. However, the way to set the X and Y axes is not limited to this. For example, as illustrated in FIG. 14, it is also possible to set the X and Y axes at a center of a rectangular test specimen, in response to a coordinate setting operation involving eight points by a user.

It is noted that the foregoing examples have been provided merely for the purpose of explanation and are in no way to be construed as limiting of the present invention. While the present invention has been described with reference to exemplary embodiments, it is understood that the words which have been used herein are words of description and illustration, rather than words of limitation. Changes may be made, within the purview of the appended claims, as presently stated and as amended, without departing from the scope and spirit of the present invention in its aspects. Although the present invention has been described herein with reference to particular structures, materials and embodiments, the present invention is not intended to be limited to the particulars disclosed herein; rather, the present invention extends to all functionally equivalent structures, methods and uses, such as are within the scope of the appended claims.

The present invention is not limited to the above described embodiments, and various variations and modifications may be possible without departing from the scope of the present invention.

What is claimed is:

1. A hardness tester for forming indentations by sequentially pressing an indenter loaded with a predetermined load against surfaces of a plurality of test specimens mounted on a test specimen stage, comprising:

a display configured to display a main screen and an assistant screen, the main screen configured to display a surface image of a test specimen of a plurality of test specimens and on which an indentation is formed by the indenter, and the assistant screen configured to display an assistant image to assist a user;

a first test location setter configured to set a test location of a first test specimen of the plurality of test specimens; and a second test location setter configured to set a test location of a second test specimen of the plurality of test specimens, the first test location setter comprising:

a first coordinate setter configured to set a reference coordinate on the surface image of the first test specimen in response to a coordinate setting operation by a user with respect to the surface image of the first test specimen when the surface image of the first test specimen is displayed on the main screen;

an indentation formation location setter configured to set a coordinate point of an indentation formation location in response to an indentation formation location setting operation by a user with respect to the surface image of the first test specimen after the reference coordinate is set by the first coordinate setter;

a setting condition store configured to store a setting condition of the coordinate point set by the indentation formation location setter; and an image store configured to store the surface image of the first test specimen displayed on the main screen, the second test location setter comprising:

an assistant image display controller configured to display the surface image of the first test specimen as the assistant image in the assistant screen when a surface image of the second test specimen is displayed on the main screen;

a second coordinate setter configured to set a reference coordinate on the surface image of the second or subsequent test specimen in response to a coordinate setting operation by a user with respect to the surface image of the second or subsequent test specimen displayed on the main screen; and an indentation formation location determiner configured to determine a coordinate point of an indentation formation location based on the reference coordinate set by the second coordinate setter and the setting condition of the coordinate point stored in the setting condition store.

2. The hardness tester according to claim 1, wherein the image store is further configured to store a surface image of the second test specimen on which an indentation is formed.

3. The hardness tester according to claim 1, further comprising a main image display controller configured to overlappingly display a location specified by the coordinate setting operation and a reference coordinate set by the first coordinate setter, on the surface image of the first test specimen displayed on the main screen.

4. The hardness tester according to claim 3, wherein the image store is further configured to store a surface image of the second test specimen on which an indentation is formed.

5. The hardness tester according to claim 3, wherein:

the image store is further configured to store the image that overlappingly displays the location specified by the coordinate setting operation and the reference coordinate set by the first coordinate setter on the surface image of the first test specimen; and the assistant image display controller displays, on the assistant screen, an image that overlappingly displays the location specified by the coordinate setting operation and the reference coordinate set by the first coordinate setter on the surface image of the first test specimen.

6. The hardness tester according to claim 5, wherein the image store is further configured to store a surface image of the second test specimen on which an indentation is formed.

* * * * *